United States Patent [19]

Gallenkamp

[11] Patent Number: 5,106,986
[45] Date of Patent: Apr. 21, 1992

[54] PREPARATION OF AMINOETHANOL DERIVATIVES

[75] Inventor: Bernd Gallenkamp, Wuppertal, Fed. Rep. of Germany

[73] Assignee: Bayer Aktiengesellschaft, Leverkusen, Fed. Rep. of Germany

[21] Appl. No.: 659,811

[22] Filed: Feb. 22, 1991

[30] Foreign Application Priority Data

Mar. 3, 1990 [DE] Fed. Rep. of Germany ....... 4006794

[51] Int. Cl.$^5$ ................. C07D 213/61; C07D 213/84
[52] U.S. Cl. ................... 546/286; 546/289; 546/310; 546/311; 546/315; 546/328
[58] Field of Search ............ 546/286, 289, 311, 315, 546/328, 310

[56] References Cited

U.S. PATENT DOCUMENTS 4,895,950  1/1990  Lindel et al. .................. 546/310

FOREIGN PATENT DOCUMENTS 0301348  2/1989  European Pat. Off. .
0305845  3/1989  European Pat. Off. .
02620781 11/1976  Fed. Rep. of Germany ...... 546/328
0657124  8/1986  Switzerland .................. 546/315

OTHER PUBLICATIONS

Chemical Abstracts, vol. 60, No. 5, Abstract 6815c, Mar. 2, 1964.
Maeda et al., "Syntheses of 2-Mercapto-4-substituted Imidazole Derivatives . . . ", Che. Pharm. Bull., vol. 32 (1984) pp. 2536-2543.

Primary Examiner—C. Warren Ivy
Assistant Examiner—Ba K. Trinh

Attorney, Agent, or Firm—Sprung, Horn Kramer & Woods

[57] ABSTRACT

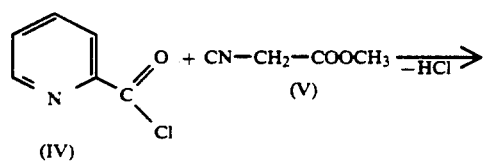

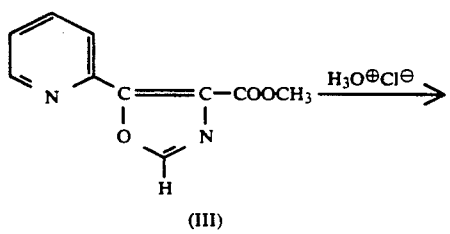

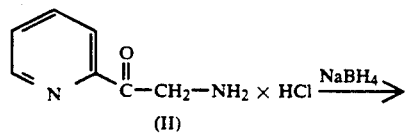

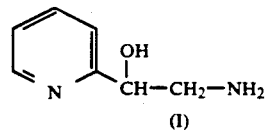

The pyridine ring may be substituted with radicals which render some compounds II and III new.

1 Claim, No Drawings

PREPARATION OF AMINOETHANOL DERIVATIVES

The present invention relates to a new process for the preparation of aminoethanol derivatives, some of which are known, new intermediate products for this process and processes for their preparation.

It is known that aminoethanol derivatives can be obtained by reduction of corresponding nitroethanol derivatives (compare Arch. Pharm. 291 (1958), 12-22; loc. cit. 292 (1959), 496-508; and loc. cit. 297 (1964), 10-30). However, nitromethane is needed for the preparation of the nitroethanol derivatives required as starting substances for this reduction, and the use of nitromethane presents major problems in industrial respects for safety reasons.

It is furthermore known that aminoethanol derivatives can also be synthesized by reaction of halogenoethanol derivatives with ammonia (compare Chem. Abstracts citation 60 (1964), 6815c); and European Patent A-244,728).

However, the yield and quality of the products obtained in this process are usually unsatisfactory.

The present invention relates to 1. a process for the preparation of aminoethanol derivatives of the general formula (I)

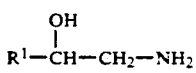

(I)

in which $R^1$ represents optionally substituted pyridyl, characterized in that aminomethyl ketones of the general formula (II)

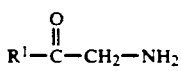

(II)

in which $R^1$ has the abovementioned meaning, or acid adducts of aminomethyl ketones of the formula (II), are reacted with hydrogenating agents, if appropriate in the presence of reaction auxiliaries and if appropriate in the presence of diluents, at temperatures between $-50°$ C. and $+150°$ C.;

2. new pyridylaminomethyl ketones of the general formula (IIa)

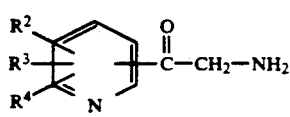

(IIa)

in which $R^2$ represents halogen or CN,
$R^3$ represents H, halogen or $NH_2$ and
$R^4$ represents H or halogen, and acid adducts of pyridylaminomethyl ketones of the formula (IIa);

3. a process for the preparation of aminomethyl ketones of the general formula (II)

(II)

in which $R^1$ represents optionally substituted pyridyl, or of acid adducts of aminomethyl ketones of the formula (II), characterized in that oxazolecarboxylic acid esters of the general formula (III)

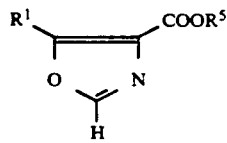

(III)

in which $R^1$ has the abovementioned meaning and
$R^5$ represents lower alkyl, are reacted with acids at temperatures between 50° C. and 100° C. in the presence of a diluent, and if appropriate the products are then liberated by treatment with strong bases;

4. new oxazolecarboxylic acid esters of the general formula (IIIa)

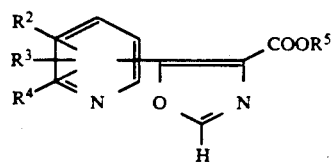

(IIIa)

in which $R^2$, $R^3$ and $R^4$ have the abovementioned meaning and
$R^5$ represents lower alkyl; and 5. a process for the preparation of oxazolecarboxylic acid esters of the general formula (III)

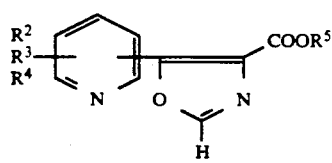

(III)

in which $R^2$, $R^3$, $R^4$ and $R^5$ have the abovementioned meanings, characterized in that carboxylic acid chlorides of the general formula (IV)

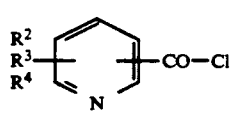

(IV)

in which $R^2$, $R^3$ and $R^4$ have the abovementioned meanings, are reacted with isocyanoacetic acid esters of the general formula (V)

$$CN-CH_2-COOR^5 \quad \text{(V)}$$

in which

R[5] has the abovementioned meaning.

in the presence of an acid acceptor and if appropriate in the presence of a diluent, at temperatures between −20° C. and +50° C.

The course of the reaction in the process steps according to the invention can be outlined, for example, by the following equation:

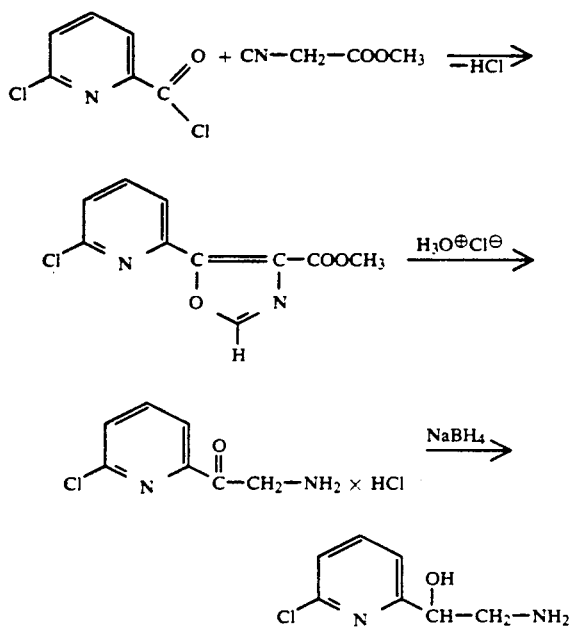

In the formulae (I) and (II), R[1] is preferably 2-pyridyl, 3-pyridyl or 4-pyridyl, each of which is optionally substituted by one to four (in particular one or two) identical or different radicals from the series comprising halogen (in particular fluorine, chlorine or bromine), $C_1$-$C_4$-alkyl (in particular methyl or ethyl), $C_1$-$C_4$-halogenoalkyl (in particular trifluoromethyl), $C_1$-$C_4$-alkoxy (in particular methoxy or ethoxy), $C_1$-$C_4$-halogenoalkoxy (in particular difluoromethoxy or trifluoromethoxy), CN, amino, $C_{1-4}$-mono- or -dialkylamino, pyrrolo, acylamino, hydroxyl, $C_{1-4}$-hydroxyalkyl and $C_{1-4}$-alkylcarbonyloxy.

In the formulae (I) and (II), R[1] particularly represents 2-pyridyl 3-pyridyl or 4-pyridyl substituted by fluorine, chlorine, bromine, CN or $NH_2$.

Acid adducts of compounds of the formula (II) are preferably the adducts with hydrogen halides, such as, for example, with hydrogen chloride, hydrogen bromide and hydrogen iodide, in particular the hydrogen chloride adducts.

Examples which may be mentioned of the compounds of the formula (I) are: 2-(2-amino-1-hydroxy-ethyl)-pyridine, 3-chloro-, 4-chloro-, 5-chloro-, 6-chloro-, 3,4-dichloro-, 3,5-dichloro-, 3,6-dichloro-, 4,5-dichloro-, 4,6-dichloro- and 5,6-dichloro-2-(2-amino-1-hydroxy-ethyl)-pyridine, 3-(2-amino-1-hydroxy-ethyl)-pyridine, 2-chloro-, 4-chloro-, 5-chloro-, 6-chloro-, 2,4-dichloro-, 2,5-dichloro-, 2,6-dichloro-, 4,5-dichloro-, 4,6-dichloro- and 5,6-dichloro-3-(2-amino-1-hydroxy-ethyl)-pyridine, 4-(2-amino-1-hydroxy-ethyl)-pyridine, 2-chloro-, 3-chloro-, 2,3-dichloro-, 2,5-dichloro-, 2,6-dichloro- and 3,6-dichloro-4-(2-amino-1-hydroxyethyl)-pyridine.

The aminoethanol derivatives of the formula (I) are known (compare the abovementioned prior art, and European Patent A-305,845 and German Patent 3,902,286 of 26.01.1989).

Examples which may be mentioned of the compounds of the formula (II) are: 2-aminoacetyl-pyridine, 3-chloro-, 4-chloro-, 5-chloro-, 6-chloro-, 3,4-dichloro-, 3,5-dichloro-, 3,6-dichloro-, 4,5-dichloro-, 4,6-dichloro- and 5,6-dichloro-2-aminoacetyl-pyridine, 3-aminoacetyl-pyridine, 2-chloro-, 4-chloro-, 5-chloro-, 6-chloro-, 2,4-dichloro-, 2,5-dichloro-, 2,6-dichloro-, 4,5-dichloro-, 4,6-dichloro-and 5,6-dichloro-3-aminoacetyl-pyridine, 4-aminoacetylpyridine, and 2-chloro-, 3-chloro-, 2,3-dichloro-, 2,5-dichloro-, 2,6-dichloro- and 3,6-dichloro-4-aminoacetylpyridine.

Some compounds of the formula (II) are known (compare J. Chem. Soc. 1938, 753–755; and Chem. Pharm. Bull. 32 (1984), 2536–2543), and in particular the compounds of the formula IIa are new.

The process according to the invention described above under 1—"process (1)"—is carried out using hydrogenating agents. The customary reducing agents which are suitable for the hydrogenation of aldehydes or ketones to alcohols can be employed.

Hydrogenating agents which may be mentioned as preferred for process (1) according to the invention are: complex hydrides, such as, for example, lithium, sodium and potassium tetrahydridoborate (borohydride or boranate and lithium, sodium and potassium tetrahydridoaluminate (alanate), hydrogen (in the presence of catalysts, compare "reaction auxiliaries") and alcoholates, such as, for example, aluminum isopropylate.

The particularly preferred hydrogenating agent for process (1) according to the invention is sodium tetrahydridoborate (sodium borohydride or sodium boranate).

Reaction auxiliaries which can be used in process (1)—in particular if hydrogen is used as the hydrogenating agent—are above all the customary hydrogenation catalysts, such as, for example, Raney nickel, palladium and platinum.

Process (1) according to the invention for the preparation of the aminoethanol derivatives of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, methyl tert.-butyl ether, glycol dimethyl ether, diglycol dimethyl ether, tetrahydrofuran and dioxane, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide; and furthermore also alcohols, such as methanol, ethanol, propanol, isopropanol, butanol, isobutanol, sec.-butanol, tert.-butanol, pentanol, isopentanol, sec.-pentanol and tert.-pentanol, and also water.

The reaction temperatures can be varied within a substantial range in process (1) according to the invention. The reaction is in general carried out at temperatures between −20° C. and +200° C., preferably at temperatures between 0° C. and 120° C.

Process (1) according to the invention is in general carried out under normal pressure. However, it is also possible for the process to be carried out under increased or reduced pressure, in general between 0.1 and 100 bar.

For carrying out process (1) according to the invention, in general between 1 and 5 mols, preferably between 1.5 and 3 mols, of hydrogenating agent are employed per mol of aminomethyl ketone of the formula (II).

The reaction components can be brought together in any desired sequence for carrying out process (1) according to the invention.

In a preferred embodiment of process (1) according to the invention, the aminomethyl ketone of the formula (II) is initially introduced into the reaction vessel in a suitable diluent and if appropriate together with a reaction auxiliary, and the hydrogenating agent is metered in according to the rate of reaction. The complete reaction mixture is further stirred until the reaction has ended and worked up by customary methods.

For example, the reaction mixture is acidified with a strong acid, such as, for example, hydrochloric acid, if appropriate diluted with an organic solvent which is virtually immiscible with water, such as, for example, methyl tert.-butyl ether, and shaken thoroughly. The aqueous phase is then separated off and concentrated to about ¼ to ½ of the volume, the concentrate is rendered alkaline with a strong base, such as, for example, sodium hydroxide solution, and the product obtained here as crystals is isolated by filtration with suction.

The compounds of the formula (IIa) are new. In the formula (IIa), the keto group is in the 2-, 3- or 4-position, preferably in the 3- or 4-position, especially preferably in the 4-position of the pyridyl ring.

$R^2$ preferably represents fluorine, chlorine, bromine or CN, and particularly preferably represents chlorine.

$R^3$ preferably represents hydrogen, chlorine or $NH_2$, particularly preferably represents chlorine or $NH_2$ and especially preferably represents chlorine.

$R^4$ preferably represents hydrogen, fluorine, chlorine or bromine, and particularly preferably represents hydrogen.

Acid adducts of compounds of the formula (IIa) are likewise preferably the adducts with hydrogen halides, such as, for example, hydrogen chloride, hydrogen bromide and hydrogen iodide, in particular the hydrogen chloride adducts.

The new aminomethyl ketones of the formula (IIa) can be prepared by the process according to the invention described above under 3—"process (3)".

Formula (III) provides a general definition of the oxazolecarboxylic acid esters to be used as starting substances in process (3) according to the invention.

In formula (III), $R^1$ preferably or in particular has that meaning which has already been given above as preferred or as particularly preferred for R in connection with the description of the compounds of the formulae (I) and (II), and $R^5$ preferably represents methyl, ethyl, propyl, isopropyl, butyl or isobutyl, in particular methyl or ethyl.

Examples which may be mentioned of the compounds of the formula (III) are: 2-(4-methoxycarbonyl-5-oxazolyl)-pyridine, 2-(4-ethoxycarbonyl-5-oxazolyl)-pyridine, 3-chloro-, 4-chloro-, 5-chloro-, 6-chloro-, 3,4-dichloro-, 3,5-dichloro-, 3,6-dichloro-, 4,5-dichloro-, 4,6-dichloro- and 5,6-dichloro-2-(4-methoxycarbonyl-5-oxazolyl)-pyridine and -2-(4-ethoxycarbonyl-5-oxazolyl)-pyridine, 3-(4-methoxycarbonyl-5-oxazolyl)-pyridine, 3-(4-ethoxycarbonyl-5-oxazolyl)-pyridine, 2-chloro-, 4-chloro-, 5-chloro-, 6-chloro-, 2,4-dichloro-, 2,5-dichloro-, 2,6-dichloro-, 4,5-dichloro-, 4,6-dichloro- and 5,6-dichloro-3-(4-methoxycarbonyl-5-oxazolyl)-pyridine and 3-(4-ethoxycarbonyl-5-oxazolyl)-pyridine, 4-(4-methoxycarbonyl-5-oxazolyl)-pyridine, 4-(4-ethoxycarbonyl-5-oxazolyl)-pyridine and 2-chloro-, 3-chloro-, 2,3-dichloro-, 2,5-dichloro-, 2,6-dichloro- and 3,6-dichloro-4-(4-methoxycarbonyl-5-oxazolyl)-pyridine and -4-(4-ethoxycarbonyl-5-oxazolyl)-pyridine.

Some of the starting substances of the formula (III) are known (compare Chem. Abstracts citation 110, 23871; and Chem. Pharm. Bull. 32 (1984), 2536–2543).

The process according to the invention described above under 3—"process (3)"—is carried out using acids. Suitable acids for process (3) are above all proton acids, such as, for example, hydrogen chloride, hydrogen bromide and hydrogen iodide. Hydrogen chloride is preferably employed as the acid in process (3).

Process (3) is carried out in the presence of a diluent. Suitable diluents are, in addition to water, above all alcohols, such as, for example, methanol, ethanol, propanol, isopropanol, butanol, isobutanol, sec.-butanol, tert.-butanol, pentanol, isopentanol, sec.-pentanol and tert.-pentanol, in particular methanol and ethanol.

The reaction temperatures can be varied within a substantial range in process (3) according to the invention. The reaction is in general carried out at temperatures between 50° C. and 100° C., preferably at temperatures between 70° C. and 95° C.

Process (3) according to the invention is in general carried out under normal pressure. However, it is also possible for the process to be carried out under increased or reduced pressure, in general between 0.1 and 10 bar.

For carrying out process (3) according to the invention, in general between 1 and 100 mols, preferably between 5 and 50 mols, of acid are employed per mol of oxazolecarboxylic acid ester of the formula (III).

The reaction components can be brought together in any desired sequence for carrying out process (3) according to the invention.

In a preferred embodiment of process (3) according to the invention, the oxazolecarboxylic acid ester of the formula (III) is initially introduced into the reaction vessel and if appropriate stirred with an alcohol. Either the acid is first added and the mixture is then brought to the required reaction temperature, or the mixture is first heated up and the acid is then metered in. The reaction mixture is stirred until the reaction has ended and is then cooled to room temperature. The product obtained as crystals (acid adduct of the compound of the formula (II)) can then be isolated by filtration with suction. Further purification of the product can be carried out by customary methods (compare the preparation examples).

The compounds of the formula (IIIa) are new.

In the formula (IIIa), $R^2$, $R^3$ and $R^4$ preferably represent the radicals which have been mentioned as preferred for the compounds of the formula IIa.

$R^5$ particularly represents methyl or ethyl.

The oxazolecarboxylic acid esters of the formula (IIIa) can thus be prepared by the process according to the invention described above under 5—"process (5)".

Formula (IV) provides a general definition of the carboxylic acid chlorides to be used as starting substances in process (5) according to the invention for the preparation of compounds of the formula (III).

In formula (IV), $R^1$ preferably or in particular has that meaning which has already been mentioned above as preferred or as particularly preferred for $R^1$ in connection with the description of the compounds of the formulae (I) and (II).

The carboxylic acid chlorides of the formula (IV) are known and/or can be prepared by processes which are known per se (compare European Patent A-244,728), under certain circumstances reactive substituents of the pyridine ring, such as $NH_2$, being protected from reaction to the acid chloride by suitable protective groups, such as the acetyl group.

Formula (V) provides a general definition of the isocyanoacetic acid esters furthermore to be used as starting substances in process (5) according to the invention. In formula (V), $R^5$ preferably or in particular has that meaning which has already been mentioned above as preferred or as particularly preferred for $R^5$ in connection with the description of the compounds of the formula (III).

The isocyanoacetic acid esters of the formula (V) are known and/or can be prepared by processes which are known per se (compare Angew. Chem. 77 (1965), 492-504; and Chem. Ber. 108 (1975), 1580-1592).

Process (5) according to the invention for the preparation of the oxazolecarboxylic acid esters of the formula (III) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide.

Acid acceptors which can be employed in process (5) according to the invention are all the acid-binding agents which can usually be used for such reactions. Preferred possible acid-binding agents are alkali metal hydrides, such as, for example, sodium hydride and potassium hydride, alkali metal alcoholates, such as sodium tert.-butylate and potassium tert.-butylate, and furthermore aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

The reaction temperatures can be varied within a substantial range in process (5) according to the invention. The reaction is in general carried out at temperatures between $-20°$ C. and $+50°$ C., preferably at temperatures between $-10°$ C. and $+40°$ C.

Process (5) according to the invention is in general carried out under normal pressure. However, it is also possible for the process to be carried out under increased or reduced pressure, in general between 0.1 and 10 bar.

For carrying out process 5) according to the invention, in general between 0.8 and 1.2 mols, preferably between 0.95 and 1.05 mols, of isocyanoacetic acid ester of the formula (V) and in general between 1 and 2 mols, preferably between 1.05 and 1.2 mols, of acid acceptor are employed per mol of carboxylic acid chloride of the formula (IV).

The reaction components can be brought together in any desired sequence for carrying out process (5).

In a preferred embodiment of process (5) according to the invention, the acid chloride of the formula (IV) is initially introduced into the reaction vessel in a diluent and the isocyanoacetic acid ester of the formula (V) is added. The acid acceptor is then slowly metered in and the reaction mixture is stirred until the reaction has ended. Working up can be carried out by customary methods.

For example, the mixture is filtered, the filtrate is concentrated to about one third of the volume by distilling off the solvent under reduced pressure and the concentrate is then diluted to about the previous volume by slow addition of water. The product of the formula (III) obtained here as crystals can be isolated by filtration with suction.

In an alternative working up process, the mixture is filtered, the solvent is distilled off from the filtrate under reduced pressure and the residue is shaken with water and an organic solvent which is virtually immiscible with water, such as, for example, ethyl acetate. The solvent is then carefully distilled off from the organic phase under reduced pressure. The residue which remains essentially contains the product of the formula (III).

The aminoethanol derivatives of the formula (I) to be prepared by the process according to the invention can be used as intermediate products for the preparation of medicaments (compare European Patent A-305,845) or growth promoters in animals (compare German Patent 3,902,286 of 26.01.1989).

PREPARATION EXAMPLES

Example 1

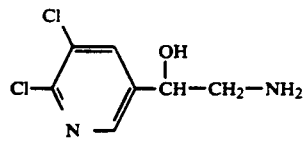

A solution of 0.9 g (24 mmol) of sodium boranate in 3 ml of water is added dropwise to a mixture, cooled to 0° C. to 5° C., of 2.85 g (12 mmol) of 5,6-dichloro-3-aminoacetyl-pyridine hydrochloride and 30 ml of methanol, while stirring. The reaction mixture is stirred at 0° C. to 5° C. for 8 hours and then concentrated under a water pump vacuum. 50 ml of water, 2 ml of acetic acid and 50 ml of ethyl acetate are added to the residue and the mixture is stirred very thoroughly. The phases are then separated and the aqueous phase is brought to pH>12 with concentrated sodium hydroxide solution, stirred thoroughly and cooled with ice. The product obtained here as crystals is isolated by filtration with suction.

1.5 g (61% of theory) of 5,6-dichloro-3-(2-amino-1-hydroxy-ethyl)-pyridine of melting point 205°-208° C. are obtained.

Example 2

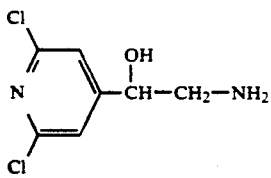

A solution of 5.7 g (0.15 mol) of sodium boranate in 25 ml of water is added dropwise to a mixture, cooled to 0° C. to 5° C., of 18.1 g (0.075 mol) of 2,6-dichloro-4-aminoacetyl-pyridine hydrochloride, 150 ml of water and 25 ml of methyl tert.-butyl ether in the course of 40 minutes, while stirring. The reaction mixture is stirred at 0° C. to 5° C. for 4 hours, 13 ml of concentrated hydrochloric acid and 50 ml of methyl tert.-butyl ether are then added dropwise and the mixture is shaken. The phases are then separated and the aqueous phase is concentrated to about one quarter of the original volume, brought to pH 12 with 26 ml of 5N sodium hydroxide solution and stirred. The product obtained as crystals is isolated by filtration with suction.

13.3 g (86% of theory) of 2,6-dichloro-4-(2-amino-1-hydroxy-ethyl)-pyridine of melting point 145° C. are obtained.

INTERMEDIATE PRODUCTS OF THE FORMULA (II)

Example (II-1)

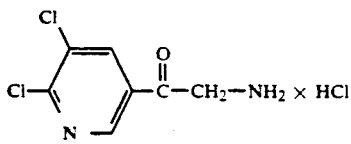

A mixture of 4.3 g (15 mmol) of 5,6-dichloro-3-(4-ethoxycarbonyl-5-oxazolyl)-pyridine and 20 ml of ethanol is heated to 80° C. and 13.5 g of concentrated hydrochloric acid are added dropwise at this temperature. The reaction mixture is heated under reflux at the boiling point for 10 hours and then concentrated, the concentrate is stirred with 10 ml of ice-water and the product is filtered off with suction.

2.85 g (79% of theory) of 5,6-dichloro-3-aminoacetyl-pyridine hydrochloride, which melts above 280° C. with decomposition, are obtained.

Example (II-2)

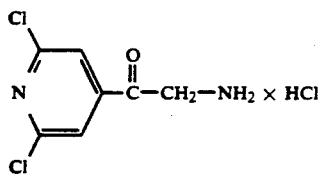

A mixture of 14.35 g (0.05 mol) of 2,6-dichloro-4-(4-ethoxycarbonyl-5-oxazolyl)-pyridine and 150 ml of concentrated hydrochloric acid is slowly heated up to 80° C. (development of foam!) and stirred at this temperature for 7 hours. After cooling, the crystalline product is separated off by filtration with suction, the residue is taken up in 150 ml of water and the mixture is filtered. The two filtrates are combined and shaken with 300 ml of toluene. The organic phase is separated off, clarified with active charcoal and filtered. The solvent is carefully distilled off from the filtrate under a water pump vacuum.

10.0 g (83% of theory) of 2,6-dichloro-4-aminoacetyl-pyridine hydrochloride are obtained as a crystalline residue of melting point 232° C.-234° C.

Example (III-3)

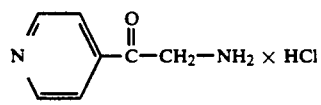

4-Aminoacetyl-pyridine hydrochloride (melting point: 268° C.-270° C./decomposition) is obtained analogously to Examples (II-1) and (II-2).

INTERMEDIATE PRODUCTS OF THE FORMULA (III)

Example (III-1)

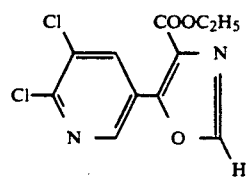

8.5 g (75 mmol) of ethyl isocyanoacetate and then 8.3 g (82 mmol) of triethylamine are added dropwise to a mixture of 15.8 g (75 mmol) of 5,6-dichloro-isonicotinoyl chloride and 100 ml of tetrahydrofuran at 20° C., while stirring. The reaction mixture is stirred at 20° C. for 17 hours and then concentrated. The residue is shaken with 400 ml of water/ethyl acetate (1/1 by volume) and the organic phase is then separated off and concentrated.

17.8 g (83% of theory) of 5,6-dichloro-3-(4-ethoxycarbonyl-5-oxazolyl)-pyridine are obtained as a crystalline residue of melting point 95° C.-98° C.

Example (III-2)

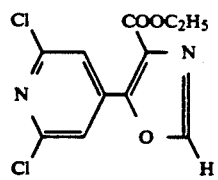

113 g (1.0 mol) of ethyl isocyanoacetate are added dropwise to a mixture of 210.5 g (1.0 mol) of 2,6-dichloro-pyridine-4-carbonyl chloride and 1.5 l of tetrahydrofuran at 0° C. to 5° C. in the course of 30 minutes and the mixture is stirred at 5° C. for 45 minutes. 111 g (1.1 mol) of triethylamine are then added dropwise at this temperature and the mixture is stirred at 20° C. for 20 hours.

The mixture is then filtered, the filtrate is concentrated to about 500 ml and about 2000 ml of water are slowly added dropwise, while stirring. The product obtained here as crystals is isolated by filtration with suction.

267 g (93% of theory) of 2,6-dichloro-4-(4-ethoxycarbonyl-5-oxazolyl)-pyridine of melting point 108° C.-109° C. are obtained.

Example (III-3)

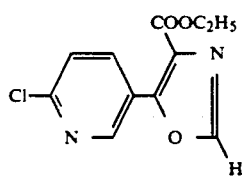

6-Chloro-3-(4-ethoxycarbonyl-5-oxazolyl)-pyridine (melting point 77° C.-79° C.) is obtained analogously to Examples (III-1) and (III-2).

Example (III-4)

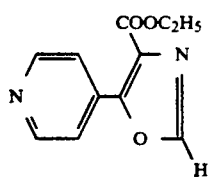

4-(4-Ethoxycarbonyl-5-oxazolyl)-pyridine (melting point 51° C.-53° C.) is obtained analogously to Examples (III-1) and (III-2).

It will be understood that the specification and examples are illustrative but not limitative of the present invention and that other embodiments within the spirit and scope of the invention will suggest themselves to those skilled in the art.

What is claimed is:

1. A pyridylaminomethyl ketone compound of the formula (IIa)

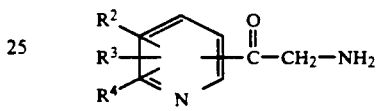

in which
$R^2$ represents halogen or CN,
$R^3$ represents H, halogen or $NH_2$ and
$R^4$ represents H or halogen,
or an acid adduct thereof.

* * * * *